(12) United States Patent
Sura

(10) Patent No.: US 9,408,582 B2
(45) Date of Patent: Aug. 9, 2016

(54) GUIDED IMAGING SYSTEM

(76) Inventor: Amish Sura, Baltimore, MD (US)

( * ) Notice: Subject to any disclaimer, the term of this patent is extended or adjusted under 35 U.S.C. 154(b) by 1268 days.

(21) Appl. No.: 13/271,226

(22) Filed: Oct. 11, 2011

(65) Prior Publication Data

US 2013/0089183 A1   Apr. 11, 2013

(51) Int. Cl.
*A61B 6/00* (2006.01)

(52) U.S. Cl.
CPC .............. *A61B 6/4225* (2013.01); *A61B 6/4441* (2013.01); *A61B 6/467* (2013.01); *A61B 6/54* (2013.01); *A61B 6/547* (2013.01); *A61B 6/548* (2013.01); *A61B 6/588* (2013.01)

(58) Field of Classification Search
CPC ..................................... A61B 6/00; A61N 5/10
See application file for complete search history.

(56) References Cited

U.S. PATENT DOCUMENTS

| | | | |
|---|---|---|---|
| 5,081,543 A | 1/1992 | Romandi | |
| 6,491,429 B1 * | 12/2002 | Suhm | A61B 6/08 378/197 |
| 6,714,841 B1 * | 3/2004 | Wright et al. | 700/259 |
| 6,747,632 B2 | 6/2004 | Howard | |
| 6,785,358 B2 | 8/2004 | Johnson | |
| 6,814,490 B1 | 11/2004 | Suhm | |
| 6,984,208 B2 | 1/2006 | Zheng | |
| 7,366,561 B2 | 4/2008 | Mills | |
| 7,377,172 B2 * | 5/2008 | Jensen et al. | 73/702 |
| 7,502,174 B2 * | 3/2009 | Jensen et al. | 359/694 |
| 7,632,014 B2 | 12/2009 | Wolfe | |
| 2004/0015075 A1 | 1/2004 | Kimchy | |
| 2004/0193413 A1 | 9/2004 | Wilson | |
| 2006/0058645 A1 | 3/2006 | Komistek | |
| 2006/0084867 A1 | 4/2006 | Tremblay | |
| 2007/0016029 A1 | 1/2007 | Donaldson | |
| 2007/0282564 A1 | 12/2007 | Sprague | |
| 2008/0004523 A1 | 1/2008 | Jensen | |
| 2008/0020332 A1 | 1/2008 | Lavenda | |
| 2008/0037701 A1 | 2/2008 | Banks | |
| 2008/0136916 A1 | 6/2008 | Wolff | |
| 2009/0110019 A1 | 4/2009 | Houde-Walter | |
| 2009/0282371 A1 | 11/2009 | Curl | |
| 2009/0306892 A1 | 12/2009 | Malka | |
| 2010/0036384 A1 | 2/2010 | Gorek | |
| 2010/0275927 A1 | 11/2010 | Saracen | |
| 2011/0026678 A1 | 2/2011 | Bonfiglio | |
| 2012/0148031 A1 * | 6/2012 | Eaves | 378/198 |
| 2013/0089183 A1 * | 4/2013 | Sura | 378/98.2 |
| 2014/0286479 A1 * | 9/2014 | Sura | 378/91 |

OTHER PUBLICATIONS

U.S. Appl. No. 61/422,615 (Dec. 13, 2010) to Eaves.*
U.S. Appl. No. 61/438,221 (Jan. 31, 2011) to Eaves.*

* cited by examiner

*Primary Examiner* — Thomas R Artman
(74) *Attorney, Agent, or Firm* — Nilay Patel

(57) ABSTRACT

Apparatus for wirelessly controlling a guided imaging system based upon the relative motion of the user. The system includes a power supply, a memory, an x-ray source, an image intensifier and a wireless transceiver coupled to the image intensifier. A separate wireless input device comprising a wireless transmitter for communicating with the wireless transceiver of the imaging system may comprise one or more sensors capable of detecting force and directional movement. This detection of movement may then be transmitted to the imaging system and translated into position signals that may direct movement and position of the image intensifier (I-I) as part of the imaging system.

16 Claims, 9 Drawing Sheets

GUIDED IMAGING SYSTEM

TECHNICAL FIELD

The present invention generally relates to medical imaging devices, more particularly, to devices for the wireless controlled movement of medical imaging equipment.

BACKGROUND OF THE INVENTION

Most interventional imaging systems use an X-ray source connected to an image intensifier (I-I) which can be utilized before, during and after a procedure. As in other medical procedures, the operator may be an assistant to the medical practitioner guided under the practitioner's directions. Typically, this requires either the operator or an assistant to physically move or adjust the imaging system using a joystick (or other manual mechanism requiring hands on) on an examination table. The medical practitioner may prefer the benefit of both controlling such an imaging system while performing the procedure. In order to operate such imaging systems, the unit is moved in various directions using hand held controls on the operating table. Movement of this device is necessary to obtain desired views of the object/patient being studied.

Potential problems with this approach include the operator having to take his hands off of the procedure to adjust the imaging, which can lead to complications of a medical error or increased time to perform the procedure. In another example, an assistant may have other responsibilities during the procedure such that repositioning the camera may introduce positional error and, similarly, prevents the assistant from concentrating on another related task. There are instances when considerable movement occurs during a critical part of the procedure, thus adding to complexity and risk of a medical error or injury to the subject.

Current operation of such imaging systems have progressed over the years to allow not only improved optical resolution and subminiature size but also improved responsiveness through the use of various user interface options such as handheld controls, joystick, mouse, or touch screen. These advances, though furthering the capacity and utility of this technology, still leave room for improvement by still sharing the common requirement to utilize the hands of the person controlling the system. This presents complications when the medical practitioner needs use of the hands for other related tasks. Therefore, as medical procedures get increasing complex there is a need for a device that can help solve or reduce the need for medical personnel to correct imaging apparatus or take away the medical personnel from the surgical treatment at hand.

In light of the foregoing considerations, and relative to the present state of the art, the need for hands-free control or guidance of I-I imaging systems remains to be sufficiently addressed. Furthermore, it remains desirable and advantageous to more efficiently maneuver such imaging systems without taking attention from other related tasks so as to create an error or risk to the subject. Finally, having a hands-free solution that can track a medical practitioner's movements, without the need for third party interaction satisfies the operators visualization requirement without having to interrupt the procedure.

SUMMARY OF THE INVENTION

It is therefore an object of the present invention to provide a wireless control device that will enable the user to guide the position of an I-I imaging system without the use of the user's hands. It is a further object of the present invention to a provide a highly responsive wireless control that may enable the user to multitask by performing an independent task with the hands while simultaneously guiding the imaging system. In one embodiment of the present invention, the wireless control mechanism that controls the guided imaging system may be mounted on the body of the user. In one embodiment of the present invention, the wireless control mechanism that controls the guided imaging system may be mounted on the head or upon a headpiece of the user. In a further embodiment of the present invention, the wireless control mechanism that controls the guided imaging system may include a voice activated control system for enabling the user to use voice commands to activate and operate the guided imaging system. The voice activated control system may comprise an audio microphone configured to receive audio or voice input commands or signals from the user, an audio receiving unit for receiving the audio or voice input commands or signals, and an audio or voice signal processor coupled to the audio receiving unit for processing the audio or voice input commands or signals. In one embodiment of the present invention, the guided imaging system may be used in a sterile environment. In a further embodiment of the present invention, the guided imaging system may be used in a healthcare facility.

In yet another embodiment of the present invention, the guided imaging system may respond similarly to that of the Nintendo Wii® controller. In one embodiment of the present invention the wireless controller may be capable of responding to direction in one or more of the following linear directions: horizontal (X), vertical (Y) and depth (Z) directions and communicate these directions to the I-I. In one embodiment of the present invention the I-I may be capable of responding to direction in one or more of the following rotational directions: pitch (rotation about the vertical axis), roll (rotation about the horizontal axis), and yaw (rotation about the depth axis). In a further embodiment of the present invention, the speed of movement of the user may be translated into the speed at which the guided imaging system, (I-I) movement, responds. The speed of movement may further accompany one of the linear directions or one or more of the rotational directions.

In another embodiment of the present invention the imaging monitors may be capable of responding to direction independently or in concert with the movement of the I-I, as shown in FIG. 3.

BRIEF DESCRIPTION OF THE DRAWINGS

The foregoing and other objects, aspects and advantages will be better understood from the following detailed description of preferred embodiments of the invention with reference to the drawings. In the drawings, like reference characters generally refer to the same parts throughout the different views. Also, the drawings are not necessarily to scale, emphasis instead generally being placed upon illustrating the principals, elements and inter-relationships of the invention.

DETAILED DESCRIPTION

Figure 1:
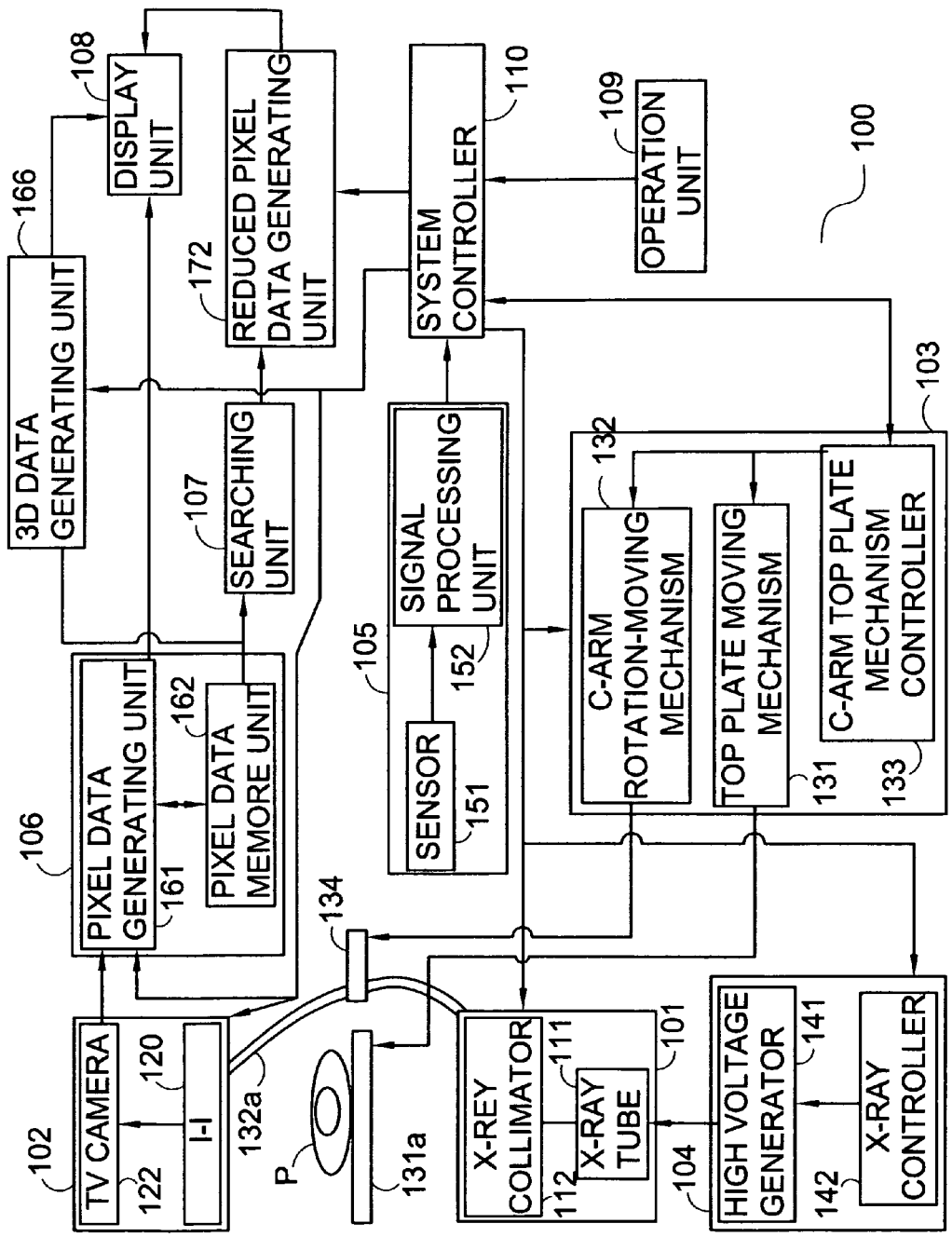
FIG. 1 is a drawing of a C-arm imaging system having an image intensifier and controllers to position both the imager and table holding the object under observation.
Figure 2:
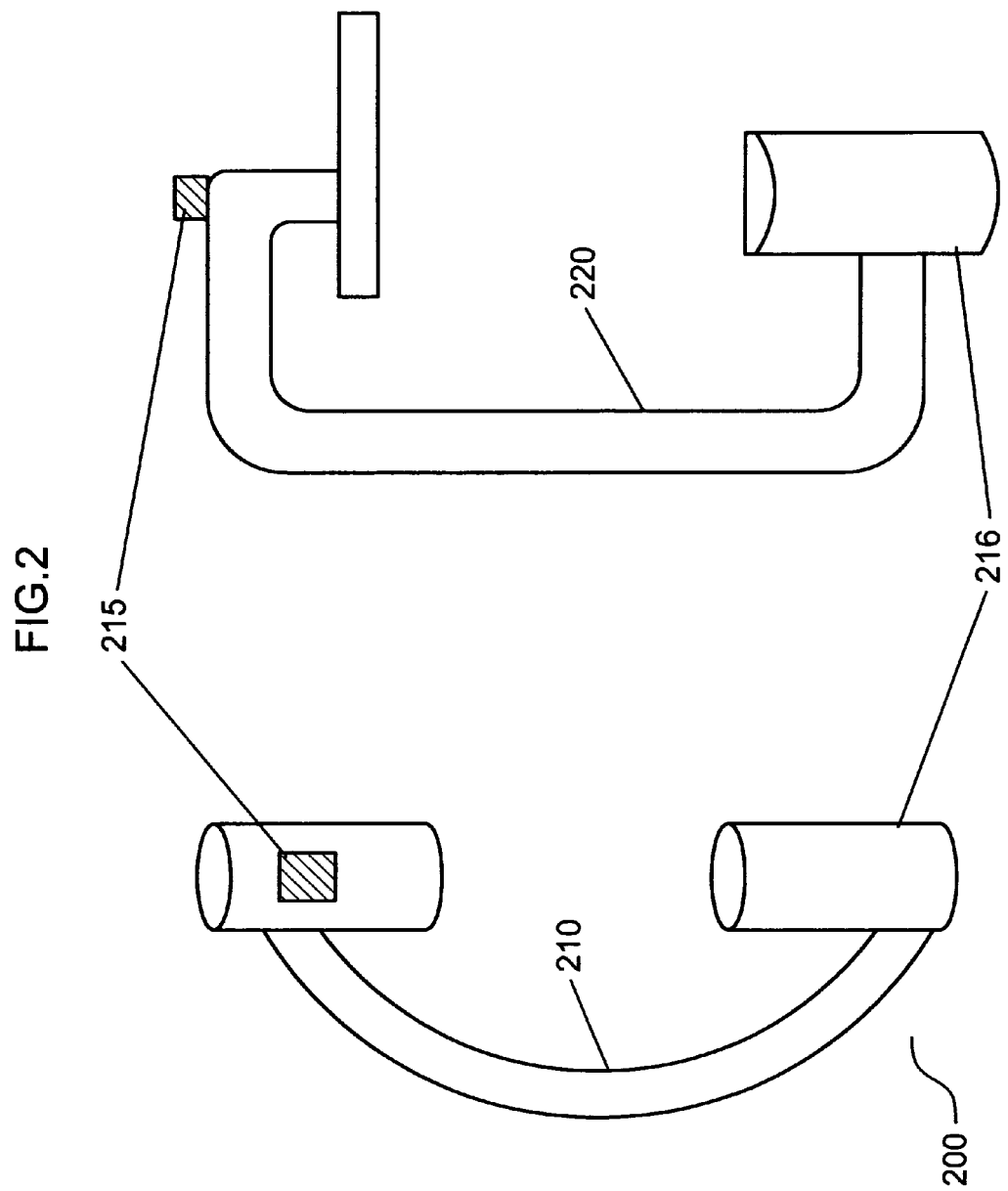
FIG. 2 is a drawing of an image system having an image sensor in multiple positions relative to the x-ray source that can include single or multiple image arrays.

FIG. 1 illustrates two configurations of an interventional guided imaging system 100, according to one embodiment of the present invention, having an x-ray source 101 opposite an image intensifier (I-I) 120. Imaging systems of this type may be moved in various directions using handheld controls on or near an examination table. Movement of the imager is necessary to obtain desired views of the object/patient under examination without the need to move object/patient. Typically, the user or an assistant will physically reposition the camera and monitors using a joystick control on the examination table. This occurs during a medical procedure, which can distract the operator from the procedure and present complications for the patient. In FIG. 2, the sensor of the image intensifier is located above a flat plane. This may include either a single or a multiple array (bi-plane) configuration.

Referring further to FIG. 1, which illustrates one embodiment of construction of a single plane type x-ray interventional guided imaging system 100 in accordance with the present invention. The x-ray interventional guided imaging system 100 includes an x-ray source 101 for irradiating x-rays onto an object P and an x-ray detecting unit 102 for collecting x-ray projection data by two dimensionally detecting x-rays penetrated through an object P. The x-ray source 101 and the penetrated x-ray detecting unit 102 are respectively supported at opposed edge portions of the C-shaped support arm 132 a. The x-ray interventional guided imaging system 100 further includes a drive unit 103 for implementing rotating movements of C-shaped support arm 132 a and position movements of top plate 131 a in order to support an object P and a high voltage generator 141. The high voltage generator 141 supplies a high voltage sufficient for production of x-rays and irradiation of x-ray to the x-ray source 101.

The drive unit 103 includes a top plate moving mechanism 131, a C-shaped support arm 132 a and a C-arm/top plate mechanism controller 133 for controlling movements of both mechanisms 131 and 132. The top plate moving mechanism 131 moves the top plate 131 a for supporting an object P along a body axis direction, a width direction of the top plate and up and down. The C-arm rotation-moving mechanism 132 performs rotation movements of C-shaped support arm 132 a around an object P. C-shaped support arm 132 a supports the x-ray source 101 and the penetrated x-ray detecting unit 102. The C-arm/top plate mechanism controller 133 controls each operations of the respective movements of the top plate moving mechanism 131 and movements or rotations of the C-arm rotation-moving mechanism 132 based on control signals supplied from the system controller 110 so as to position an imaging object, such as blood vessel, and x-ray radiation unit at a plurality of different angle positions in order to perform x-ray radiography at appropriate angle positions while avoiding obstacles, such as bones, as explained later.

The top plate moving mechanism 131 includes a sensor (not shown), such as an encoder, for detecting a moved distance of the top plate 131a. C-arm/top plate mechanism controller 133 controls the top plate moving mechanism 131 based on the detected signals supplied from the moved distance sensor. The top plate moving mechanism 131 moves the top plate 131 a so as to set it at desired positions based on the control signals from the C-arm/top plate mechanism controller 133. Similarly, C-arm rotating-moving mechanism 132 includes a rotating angle sensor (not shown), such as an encoder for detecting rotated angles of the C-shaped support arm 132 a. C-arm rotation-moving mechanism 132 rotates the C-shaped support arm 132 a under control from the C-arm/top plate mechanism controller 133 based on the angle position of the detected living body. By the rotations of the C-shaped support arm 132 a, a pair of the x-ray interventional guided imaging system 100 and the x-ray detecting units 102 are positioned at desired radiography angle positions and distances based on the controlling signals from the C-arm/top plate mechanism controller 133. When the C-shaped support arm 132 a is positioned at a desired position, the C-arm rotation-moving mechanism 132 supplies an angle positioned signal of the positioned radiography angle position to the system controller 110.

The x-ray interventional guided imaging system 100 includes an x-ray tube 111 for generating x-rays and an x-ray collimator 112. The x-ray collimator 112 restricts an x-ray irradiation area over an object P from the x-ray tube 111. A high voltage generating unit 104 supplies a high voltage to the x-ray tube 111 in x-ray interventional guided imaging system 100. The high voltage generating unit 104 includes a high voltage generator 141 and an x-ray controller 142 that controls the high voltage generator 141 based on control signals supplied from a system controller 110.

X-ray detecting unit 102 includes an image intensifier (I.I.) 120 that detects x-rays penetrated through an object P and converts the penetrated x-rays to light signals, a television (TV) camera 122 for converting the light signals to electric signals and an analog-to-digital (A/D) converter (not shown) for converting electric signals from the TV camera 122 to digital signals. X-ray projection data converted to digital signals are thereby supplied to a pixel data processing unit 106. I.I. 120 includes a moving mechanism so as to move its positions forward and backward so as to face the x-ray interventional guided imaging system 100. Thus, a distance between the x-ray generating source and the x-ray detector (Source to Detector Distance: SDD) can be adjusted. Further adjustment can be made to the x-ray incidence view size (Field Of View: FOV) by controlling electric voltages of an x-ray receiving surface electrode of I.I. 120. In this embodiment, an I.I. is illustrated as a detector. It is, of course, possible to apply a plate surface type detector (Flat Panel Detector: FPD) in order to convert the detected x-rays to electric charges.

Pixel data processing unit 106 generates pixel data from x-ray projection data that are generated in the x-ray detecting unit 102. The generated pixel data are stored. Thus, the pixel data processing unit 106 includes a pixel data generating unit 161 for generating pixel data and a pixel data memory unit 162 for storing the generated pixel data. Pixel data generating unit 161 generates pixel data in accordance with x-ray radiography data being supplied from the detector 102 and managing vital data of an object P being supplied from a vital data measuring unit 105 through a system controller 110. The vital data measuring unit 105 includes a sensor 151 for detecting and measuring various physiological statistics of object P, and a signal processing unit 152 for converting and processing the measured various physiological statistics in vital data for pixel data generating unit 161. The generated pixel data are stored in a pixel data memory unit 162.

Pixel data that are collected, which include at least at two different angle positions and stored in the pixel data memory unit 162, are supplied to a three dimensional image generating unit 166. The three dimensional image generating unit 166 generates three dimensional image data from pixel data collected at least at two different positions. To generate three dimensional image data, vital data are supplied from a vital data measuring unit 105 through the system controller 110 in order to select pixel data of the same phase of at least two different positions. The generated three dimensional data is displayed on a display unit 108.

The interventional guided imaging system 100 further includes a pixel data searching unit 107 for searching a plurality of pixel data stored in the pixel data memory unit 162. Pixel data searching unit 107 searches for a plurality of pixel data of the same phase among a plurality of pixel data stored in the pixel data memory unit 162, and a reduced pixel data generating unit 172 generates reduced pixel data from the searched pixel data of the same phase. A plurality of sets of the generated reduced pixel data of the same phase are displayed on a screen of a display unit 108. Thus, either a plurality of sets of pixel data of the same phase that are generated in the three dimensional image data generating unit 166 or a plurality of sets of reduced pixel data reduced of the same phase that are generated in the pixel data generating unit 172 are displayed on the display unit 108.

The interventional guided imaging system 100 further includes an operation unit 109 for inputting various setting conditions or commands. The operation unit 109 designates various inputs of radiography conditions, such as, input operations of an object ID, such as a name of an object P and respective times of radiography, image magnifying ratio, designation of setting positions of the C-arm, designation of setting position of radiography angles, designation of setting position of the top plate, and a selection of static images or successive images that are collected at a time series during a certain time period (hereinafter, simply referred to as "a motion image"), and various conditions for displaying. In order to select a motion image, the operation unit 109 further inputs additional radiography conditions of a frame rate indicating a frame number in a unit time and an irradiation time. The system controller 110 totally controls the overall operation of the apparatus in accordance with the inputted conditions from the operation unit 109.

FIG. 2 illustrates an image system 200 having an image sensor in mountable positions relative to the x-ray source, according to one embodiment of the present invention. Such configurations may include single or multiple image arrays. C-arm imaging system 210 includes a C-shaped support arm which contains both the I-I and sensor 215 at the top to communicate with an external position controller (not shown). G-Image system 220 includes a support arm similar in function to the C-shaped support arm of C-Image system 210, however, having a planar vertical surface extending between the I-I with sensor 215 and the x-ray source 216. Such configurations may include either flat plane or adjustable plane mechanisms.

Figure 3:
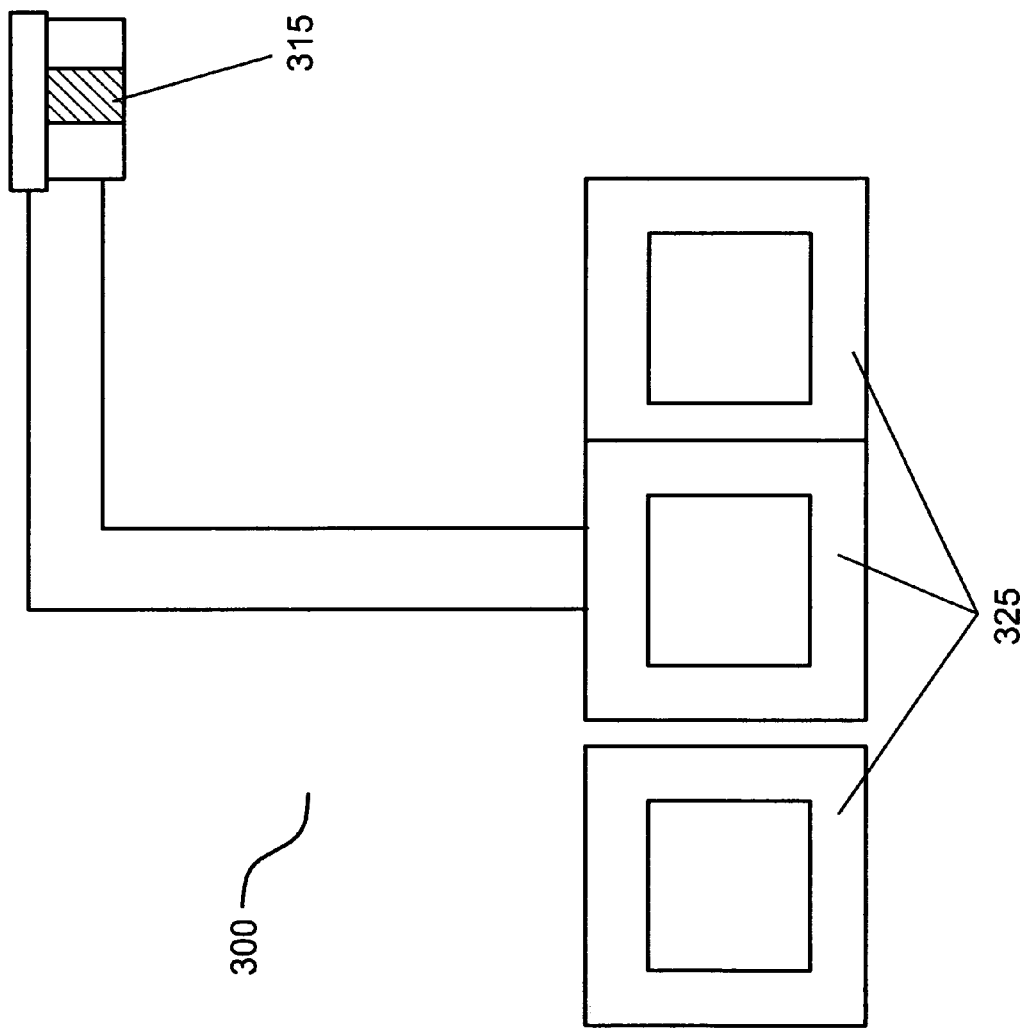
FIG. 3 is a drawing of an image system mountable from a wall or ceiling that incorporates monitors and having a swivel adjustable sensor.

FIG. 3 illustrates a ceiling mountable guided imaging system 300, having a swivel mount sensor 315 and adjacent multiple monitors 325, according to one embodiment of the present invention. In this configuration, the sensing of rotational directions on the user-worn wireless transmitter (not shown) sends communication signals to the swivel mount sensor 315, which may implement rotational or linear movement of the multiple monitors 325.

Figure 4:
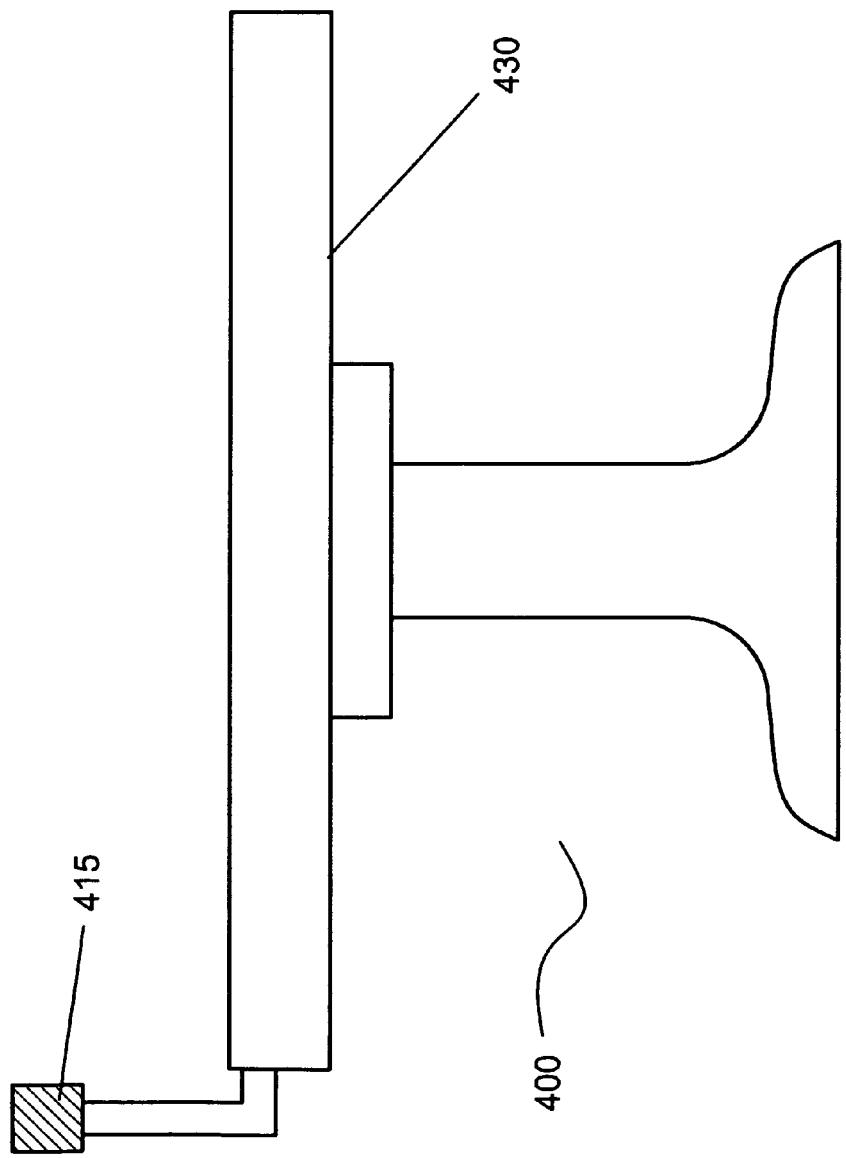
FIG. 4 is a drawing of an image system having an image sensor mountable on an examination table.

FIG. 4 illustrates a table-mounted guided imaging system 400, according to one embodiment of the present invention, in which the I-I and sensor 415 mounts on the side of the examination/observation table 430. The I-I and sensor 415 points horizontally across the plane of the table 430 toward an x-ray source (not shown).

Figure 5:
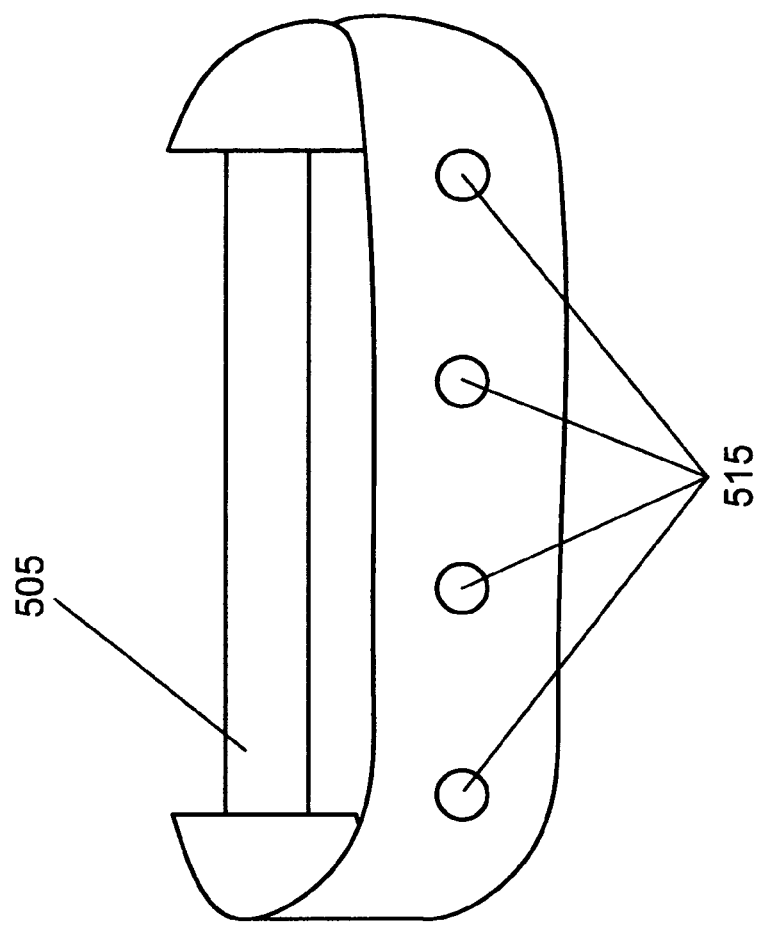
FIG. 5 is a drawing of a headband mountable device having a wireless transmitter and sensors built therein.

FIG. 5 is a drawing of a head-mountable wireless controller 500. In this configuration, the control device includes an elastic membrane 505 on a first side opposite a second side which may contain one or more sensors 515. The sensors 515 also send communications to the system controller 110 for controlling movements of both the top plate moving mechanism 131, and the C-arm rotation-moving mechanism 132, by the C-arm/top plate mechanism controller 133, including, for example, implementing rotating movements of C-shaped support arm 132 a and position movements of top plate 131 a, as described above. The sensors 515 also send communications to the system controller 110 for controlling the multiple monitors 325 as described above. Motion of the head may direct motion of the imaging system 500 and monitors 325 either independently or on concert with one another.

It is within the scope of this invention that a control mechanism such as a switch or button on the wireless embodiments that will allow the user to differentiate commands from the position or movement of the user to one or more controlled systems (e.g., remotely controlling the C-arm imaging system 210 or the multiple monitors 325 or individual I-I's in a multi-plane system). The sensors 515 may comprise the ability to sense position or movement in one or more of the following linear directions: horizontal (X), vertical (Y) and depth (Z) directions. In one embodiment of the present invention the wireless controller 500 may comprise sensors 515 capable of sensing movement in one or more of the following rotational directions: pitch (rotation about the vertical axis), roll (rotation about the horizontal axis), and yaw (rotation about the depth axis). One example of this type of wireless control response is that of the Nintendo Wii® controller used with the Nintendo Wii® game system. This design concept utilizes accelerometers that allow the wireless controller to detect the motion of the controller. The motion is communicated to the I-I which is translated into motion of the imaging system 210 and may be used to position the I-I or monitors 325 or both. There are also tiny silicon springs inside the controller that detect motions, positions, and tilt. The wireless communication between the handheld unit and console is infrared. Although infrared is common in industry as a wireless communication protocol, there are several others which are contemplated to be used in the present invention. Some examples include Bluetooth, wireless fidelity radio frequency (also known as WiFi) which follows IEEE standard 802.11a/b/g/n and cellular frequencies. Some RF wireless modules available on the market include Linx Technologies LT, LR and LC Series transceivers. These provide either uni-directional or bi-directional communication with serial data and command signals.

In a further embodiment of the present invention, the sensors 515 may be capable of sensing speed of movement of the user. This sensed speed may then be translated into the speed at which the guided imaging system 100 responds to movement by the user.

Figure 6:
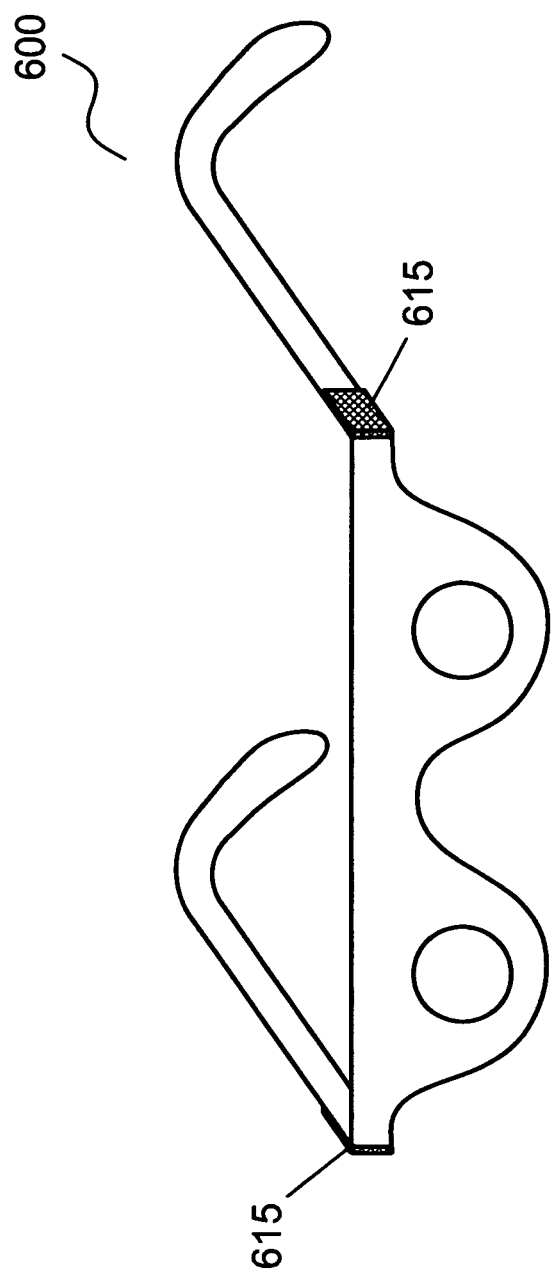
FIG. 6 is a drawing of a wireless controller for an image system that is attachable to eyewear of the user.

FIG. 6 is a drawing of a head-mountable wireless controller 600, according to one embodiment of the present invention. In this configuration, the control device includes sensors 615 which may be attachable to the eyewear of the user. Eyewear may include eyeglasses, safety glasses/goggles or other eyewear commonly utilized while operating an imaging system.

Figure 7:
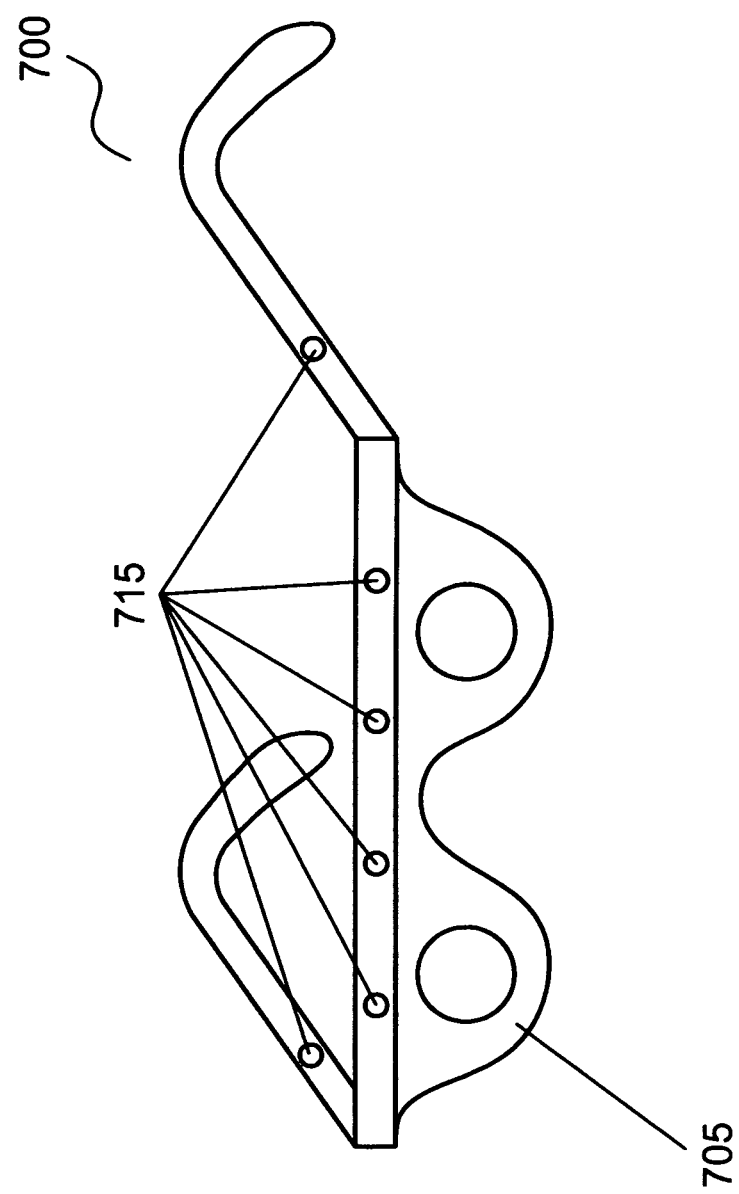
FIG. 7 is a drawing of a wireless controller for an image system that is built into eyewear.

FIG. 7 is a drawing of a head-mountable wireless controller 700, according to one embodiment of the present invention. In this configuration, the control device includes eyewear 705 comprising sensors 715 mounted or molded into the frame of the eyewear 705. Similarly, as contemplated in the example of FIG. 6, this embodiment can be utilized in a variety of types of eyewear.

Figure 8:
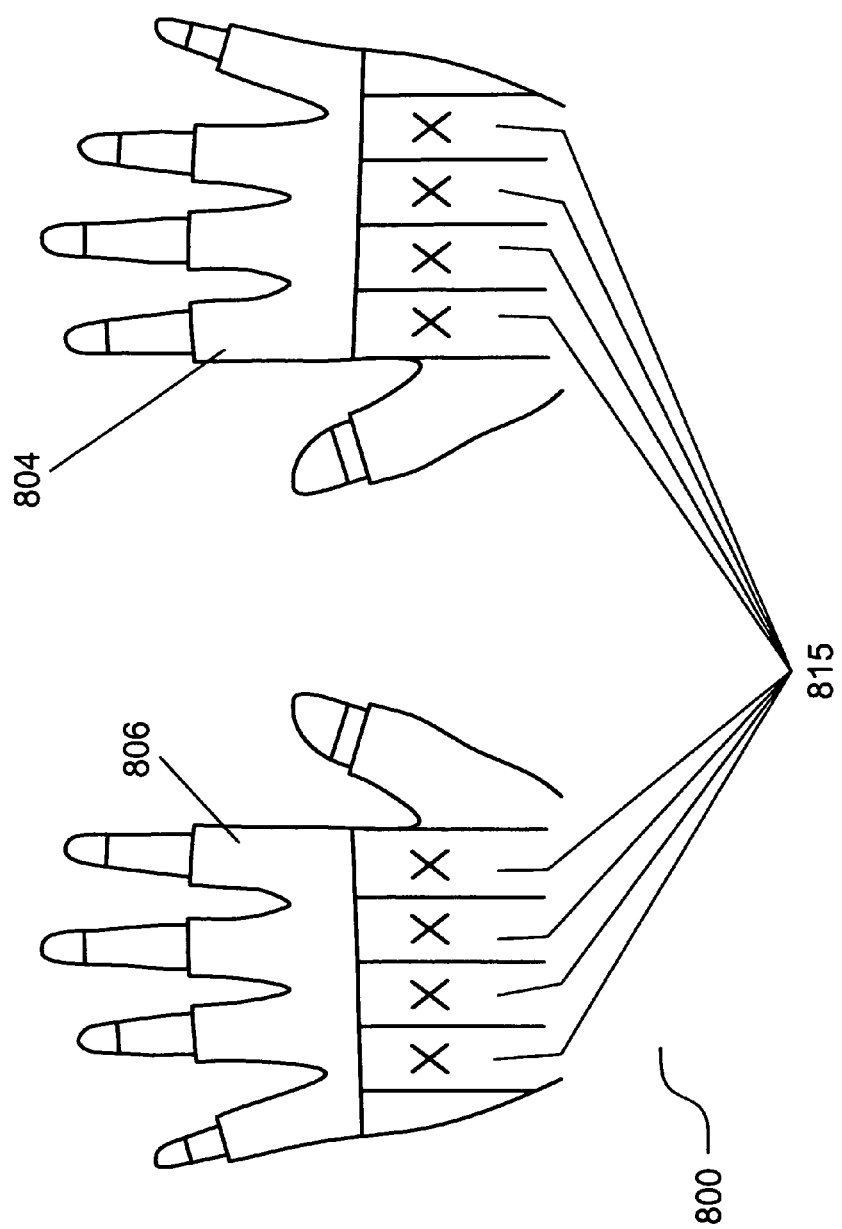
FIG. 8 is a drawing of a wireless controller for an image system that is built into gloves.

FIG. 8 illustrates a glove-mounted wireless controller 800, according to one embodiment of the present invention. In this embodiment, either the dorsal side 804 or the palm side 806 of the glove-mounted controller 800 comprise sensors 815. It is contemplated that even both sides of the glove-mounted wireless controller 800 may comprise sensors 815 capable of linear or rotational direction as well as speed sense.

Figure 9:
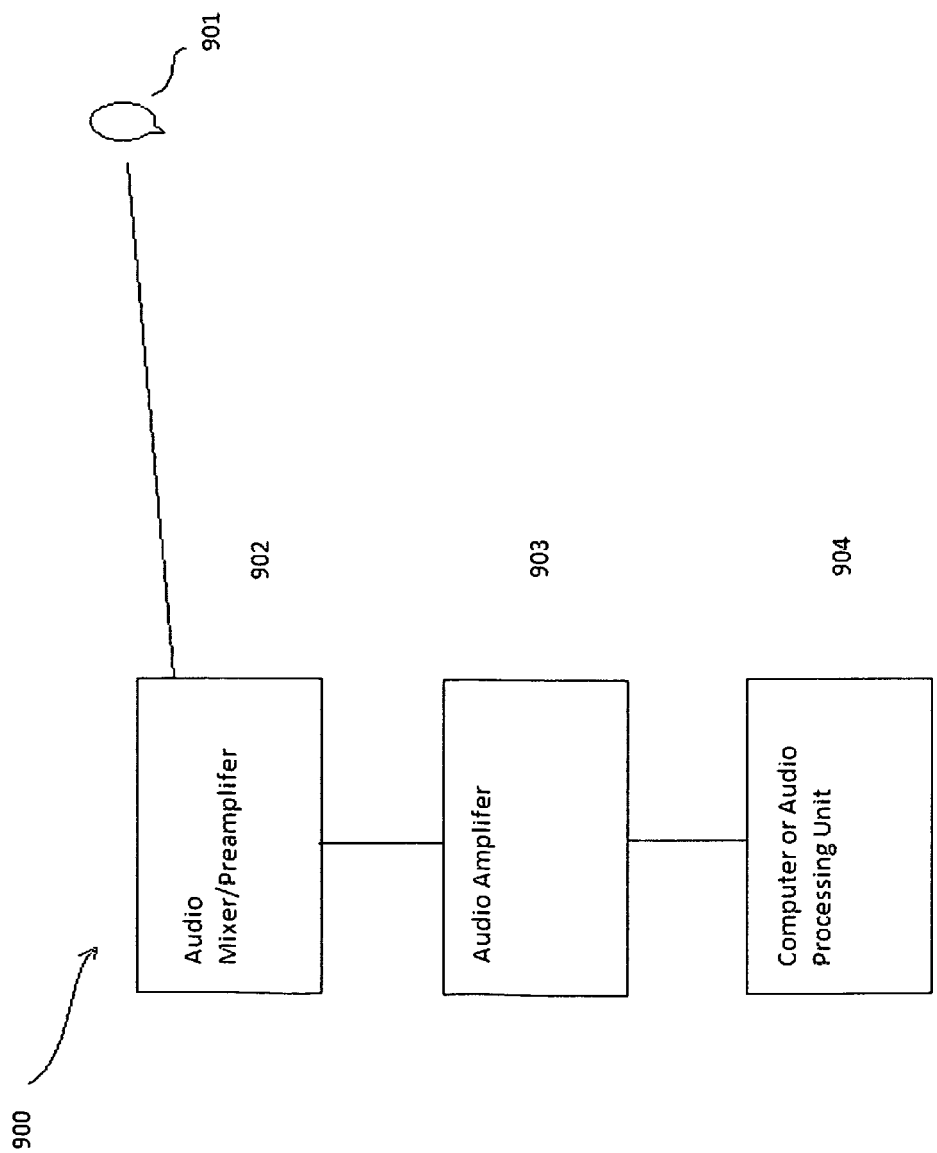
FIG. 9 is a drawing of a voice activating system.

FIG. 9 is a drawing of a voice activated system 900, according to one embodiment of the present invention. In this configuration, a microphone 901 is coupled to an audio mixer/preamplifier 902. Embodiments of the microphone 901 may include a wired microphone, a wireless microphone, or a shotgun microphone which allows the user to be move about without being tethered to by wires or cables, or without wearing a wireless microphone system. The voice activated system 900 further includes an audio amplifier 903 coupled to the audio mixer/preamplifier 902. Audio mixer/preamplifier 902 and audio amplifier 903 are coupled to an audio processing unit 904. Audio processing unit 904 may be communicatively coupled to the I-I or monitors 325 or both. The means of communication between the audio processing unit 904 and the I-I or monitors 325 or both may include Bluetooth, wireless fidelity radio frequency (also known as WiFi) which follows IEEE standard 802.11a/b/g/n and cellular frequencies. Examples of the audio processing unit 904 may include a computer comprising a memory and a processor. Audio processing unit 904 may operate under the control of voice recognition software. The voice control system recognizes a series of key words which corresponds to a command or series of commands that may otherwise be initiated through manual commands or controls. After recognition, the voice control system may repeat the recognized command or series of commands, and execute the command. The command or series of commands are communicated to the I-I which is translated into motion of the imaging system 210 and may be used to position the I-I or monitors 325 or both. Operations controlled by the voice activated control system may include directing the guided imaging system, (I-I), in one or more of the following linear directions: horizontal (X), vertical (Y) and depth (Z) directions, directing the I-I in one or more of the following rotational directions: pitch (rotation about the vertical axis), roll (rotation about the horizontal axis), and yaw (rotation about the depth axis), and adjusting the speed at which the I-I moves at one of the linear directions or one or more of the rotational directions. Operations controlled by the voice activated control system may also include directing the imaging monitors independently or in concert with the movement of the I-I. Operations controlled by voice activated control system may also include designation of various inputs of radiography conditions, such as, input operations of an object ID, such as a name of an object and respective times of radiography, image magnifying ratio, designation of setting positions of the C-arm, designation of setting position of radiography angles, designation of setting position of the top plate, and a selection of static images or successive images that are collected at a time series during a certain time period, and various conditions for displaying.

There are other variations or variants of the described methods of the subject invention which will become obvious to those skilled in the art. It will be understood that this disclosure, in many respects is only illustrative. Although various aspects of the present invention have been described with respect to various embodiments thereof, it will be understood that the invention is entitled to protection within the full scope of the appended claims.

What is claimed is:

1. A device for remote motion control of an imaging system, comprising:
 a power supply;
 a memory;
 an x-ray source;
 an image intensifier (I-I);
 a wireless transceiver coupled to said image intensifier;
 a wireless input device further comprising a wireless transmitter communicatively coupled to said wireless transceiver and said wireless input device that reads a force sensor and a position sensor.

2. The device for remote motion control of an imaging system, of claim 1 wherein said force sensor and said position sensor are capable of sensing at least one or more of the group comprising vertical, horizontal and depth.

3. The device for remote motion control of an imaging system, of claim 2 wherein said force sensor and said position sensor are sensitive to speed of motion.

4. The device for remote motion control of an imaging system, of claim 2 wherein said force sensor and said position sensor are sensitive to speed of motion comprising a roll, a pitch and a yaw.

5. The device for remote motion control of an imaging system, of claim 1 wherein said force sensor and said position sensor are capable of sensing at least a roll, a pitch and a yaw of said image intensifier (I-I).

6. The device for remote motion control of an imaging system, of claim 1, further comprising an attachable mounting device, said wireless input device coupled to the attachable mounting device, wherein said attachable mounting device is capable of being attached to a user.

7. The device for remote motion control of an imaging system, of claim 1, wherein said wireless transceiver is additionally coupled to one or more monitors.

8. An medical imaging system comprising:
 an x-ray imaging source, a power supply, a memory, an image intensifier (I-I), a wireless transceiver, a wireless transceiver interface, a wireless input device comprising a wireless transmitter communicatively coupled to said wireless transceiver interface;
 said wireless input device includes force and position sensors; and
 said force and position sensors further capable of sensing speed of motion.

9. The medical imaging system of claim 8 wherein said force and position sensors are capable of sensing one or more of the group comprising vertical position, horizontal position and depth position.

10. The wireless input device of claim 8 wherein said force and position sensors are capable of sensing one or more of the group comprising rotational roll, rotational pitch and rotational yaw.

11. The wireless input device of claim 8, further comprising an attachable mounting device, said wireless input device coupled to the attachable mounting device, wherein said attachable mounting device is capable of being attached to a user.

12. A method for wirelessly controlling a medical x-ray imaging system comprising the steps of:

transmitting at least one control parameter from a wireless input device wherein said control parameter comprises includes force, position and speed;

receiving said control parameter from said wireless input device;

translating said control parameter into a position of an image intensifier of said medical x-ray imaging system; and moving said image intensifier based on said translating.

13. The system of claim 12 wherein said force and position sensors are capable of sensing one or more of the group comprising vertical position, horizontal position and depth position.

14. The system of claim 12 wherein said force and position sensors are capable of sensing one or more of the group comprising roll, pitch and yaw.

15. The system of claim 12, further comprising an attachable mounting device, said wireless input device coupled to the attachable mounting device, wherein said attachable mounting device is capable of being attached to a user.

16. A device for remote motion control of an imaging system, comprising:
a power supply;
a memory;
an x-ray source;
an image intensifier (I-I);
a wireless transceiver coupled to said image intensifier;
a wireless input device further comprising a wireless transmitter communicatively coupled to said wireless transceiver and said wireless input device that reads a force sensor and a position sensor; whereby said force sensor and said position sensor are capable of sensing at least one or more of the group comprising x-coordinate, y-coordinate and z-coordinate.

* * * * *